(12) United States Patent
Su

(10) Patent No.: US 7,067,262 B2
(45) Date of Patent: Jun. 27, 2006

(54) CELL LINE FOR THE EXPRESSION OF AN α2δ2 CALCIUM CHANNEL SUBUNIT AND METHODS OF USE

(75) Inventor: Ti-Zhi Su, Ann Arbor, MI (US)

(73) Assignee: Warner Lambert Company LLC, Morris Plains, NJ (US)

( * ) Notice: Subject to any disclaimer, the term of this patent is extended or adjusted under 35 U.S.C. 154(b) by 321 days.

(21) Appl. No.: 10/258,936

(22) PCT Filed: May 8, 2001

(86) PCT No.: PCT/US01/14799

§ 371 (c)(1),
(2), (4) Date: Jan. 22, 2003

(87) PCT Pub. No.: WO01/88101

PCT Pub. Date: Nov. 22, 2001

(65) Prior Publication Data

US 2003/0212132 A1    Nov. 13, 2003

Related U.S. Application Data

(60) Provisional application No. 60/204,466, filed on May 16, 2000.

(51) Int. Cl.
*G01N 33/53*    (2006.01)
*G01N 33/567*   (2006.01)
*C12N 5/00*     (2006.01)
*C12N 5/02*     (2006.01)

(52) U.S. Cl. .......................... 435/7.2; 435/325
(58) Field of Classification Search ................ 435/7.2, 435/325, 69.1, 252.3, 471
See application file for complete search history.

(56) References Cited

FOREIGN PATENT DOCUMENTS

WO    9639512    12/1996
WO    9908670    2/1999

OTHER PUBLICATIONS

Gao et al., "Functional Properties of a New Voltage-dependent Calcium Channel alpha2delta Auxiliary Subunit Gene (CACNA2D2)", *The Journal of Biological Chemistry*, vol. 275, No. 16, 2000, pp. 12237-12242.

Klugbauer et al., "Molecular Diversity of the Calcium Channel alpha2delta Subunit", *The Journal of Neuroscience*, vol. 19, No. 2, 1999, pp. 684-691.

Gee et al., "The Novel Anticonvulsant Drug, Gabapentin (Neurontin), Binds to the alpha2delta Subunit of a Calcium Channel", *The Journal of Biological Chemistry*, vol. 271, No. 10, 1996, pp. 5768-5776.

Suman-Chauhan et al., "Characterization of [3H]gahapentin binding to a novel site in rat brain: homogenate binding studies", *European Journal of Pharmacology—Molecular Pharmacology Section*, vol. 244, 1993, pp. 293-301.

Su et al., "Human alpha2delta2 subunit of calcium channel: a novel gabapentin binding protein in rat", *Society for Neuroscience Abstracts*, vol. 26, No. 2, 2000, Abstract No. 40.20.

*Primary Examiner*—Robert S. Landsman
(74) *Attorney, Agent, or Firm*—Mehdi Ganjeizadeh; Charles W. Ashbrook

(57) ABSTRACT

Described is a method for determining the binding ability of a compound to bind to an α2δ2 subunit of a calcium channel comprising: providing an α2δ2 subunit of a calcium channel, contacting the subunit with the compound, and determining the binding ability of the compound to bind to the subunit.

12 Claims, 10 Drawing Sheets

FIG. 1 CLONING OF HUMAN α2δ2.

FIG. 7
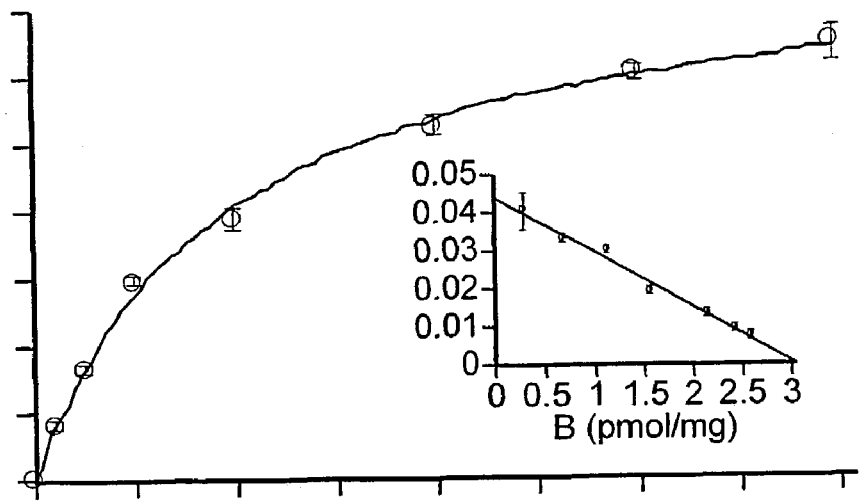
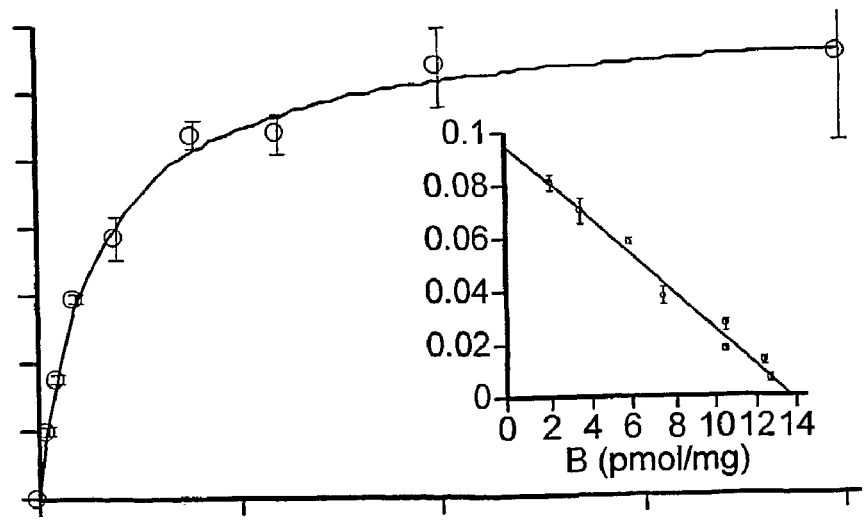

SEQUENCE LISTING

<160> NUMBER OF SEQ ID NOS: 14

<210> SEQ ID NO 1
<211> LENGTH: 24
<212> TYPE: DNA
<213> ORGANISM: Homo sapiens

<400> SEQUENCE: 1
tcttgaatgg aaacatggcg gtgc                                          24

<210> SEQ ID NO 2
<211> LENGTH: 24
<212> TYPE: DNA
<213> ORGANISM: Homo sapiens

<400> SEQUENCE: 2
tataccaggg tctccttcgg acat                                          24

<210> SEQ ID NO 3
<211> LENGTH: 24
<212> TYPE: DNA
<213> ORGANISM: Homo sapiens

<400> SEQUENCE: 3
atgtgttcat ggaaaaccgc agac                                          24

<210> SEQ ID NO 4
<211> LENGTH: 24
<212> TYPE: DNA
<213> ORGANISM: Homo sapiens

<400> SEQUENCE: 4
agccgttcag gtcaatggca aaca                                          24

<210> SEQ ID NO 5
<211> LENGTH: 24
<212> TYPE: DNA
<213> ORGANISM: Homo sapiens

<400> SEQUENCE: 5
ccatccgcat caacacacag gaat                                          24

<210> SEQ ID NO 6
<211> LENGTH: 24
<212> TYPE: DNA
<213> ORGANISM: Homo sapiens

<400> SEQUENCE: 6
gtaagtcctc attgttaacc tcgc                                          24

<210> SEQ ID NO 7
<211> LENGTH: 24
<212> TYPE: DNA
<213> ORGANISM: Homo sapiens

<400> SEQUENCE: 7
ctgagaagtt caaggtgcta gcca                                          24

<210> SEQ ID NO 8
<211> LENGTH: 24
<212> TYPE: DNA
<213> ORGANISM: Homo sapiens

-continued

```
<400> SEQUENCE: 8
gatgtgattt gggtgccaaa cacc                                              24

<210> SEQ ID NO 9
<211> LENGTH: 24
<212> TYPE: DNA
<213> ORGANISM: Homo sapiens

<400> SEQUENCE: 9
gacgcggtga ataatatcac agcc                                              24

<210> SEQ ID NO 10
<211> LENGTH: 24
<212> TYPE: DNA
<213> ORGANISM: Homo sapiens

<400> SEQUENCE: 10
acaaatcgtg ctttcactcc cttg                                              24

<210> SEQ ID NO 11
<211> LENGTH: 24
<212> TYPE: DNA
<213> ORGANISM: Homo sapiens

<400> SEQUENCE: 11
ctgagaagtt caaggtgcta gcca                                              24

<210> SEQ ID NO 12
<211> LENGTH: 24
<212> TYPE: DNA
<213> ORGANISM: Homo sapiens

<400> SEQUENCE: 12
gatgtgattt gggtgccaaa cacc                                              24

<210> SEQ ID NO 13
<211> LENGTH: 24
<212> TYPE: DNA
<213> ORGANISM: Homo sapiens

<400> SEQUENCE: 13
cgtgtccttg gcagatgaat ggtc                                              24

<210> SEQ ID NO 14
<211> LENGTH: 24
<212> TYPE: DNA
<213> ORGANISM: Homo sapiens

<400> SEQUENCE: 14
catctcagtc agtgtcacct tgag                                              24
```

CELL LINE FOR THE EXPRESSION OF AN α2δ2 CALCIUM CHANNEL SUBUNIT AND METHODS OF USE

This application claims the benefit of PCT/US01/14799 filed May 8, 2001, which claims the benefit of U.S. Provisional Application 60/204,466 filed May 16, 2000; the entire contents of each of which are hereby incorporated herein by reference.

FIELD OF THE INVENTION

This invention pertains to cell lines which express an α2δ2 subunit of a voltage-dependent calcium channel, where the cell lines may also express additional calcium channel subunits, and where the binding of gabapentin, gabapentin analogues, pregabalin, or pregabalin to the cells may be determined.

BACKGROUND OF THE INVENTION

Voltage-dependent calcium channels have been linked to physiological processes such as neurotransmitter release, secretion of hormones, muscle contraction, and regulation of gene transcription. A functional channel requires at least three subunits, including the α1, α2δ and β subunits. The channel may also contain a γ subunit. There are several known types of voltage-dependent calcium channels that have been defined based on their electrophysiological characteristics and pharmacological properties. These types are L-, N-, P/Q-, R-, and T-type. Each type is primarily defined by its channel composition. The type of α1 subunit contained in the channel determines whether the channel is an L-, N-, P/Q-, R-, or T-type channel. The activity of the α1 subunit is modulated by the α2δ and β subunits. Channel activity may be further modulated by a fourth subunit, γ.

Molecular biological techniques have allowed elucidation of the mechanism of voltage-dependent calcium channel action. Genes for each of the subunits have been isolated and cloned. There are currently nine known genes encoding for different α1 subunits. The α1 subunit forms the pore which calcium ions flow through. The α1 subunit contains the voltage sensor and is also responsible for the binding specificity of certain drugs or toxin that may be associated with the channel type. Channel current through the α1 pore may be modulated by association of the β, γ, or α2δ subunit. There are four known genes for the intracellular β subunit that may be differentially spliced. There are two known genes for the transmembrane γ subunit, one in skeletal muscle and a novel gene expressed in the brain. Only one isoform of α2δ was initially identified. Recently, however, two new α2δ genes were identified, α2δ2 and α2δ3. These genes have 55.6 and 30.3% homology with the original α2δ1 gene (Klugbauer, et al., *J Neuroscience* 1999;19(2): 684–691). The α2 and δ proteins are expressed by the same gene. The protein product is post-translationally cleaved, and the final. α2 and δ proteins are linked by disulfide bonds. The transmembrane δ protein secures the α2 protein to the cell membrane.

Studies have shown that the α2δ1 subunit contains a binding site for the anticonvulsant drug, gabapentin [1-(aminomethyl)cyclohexane acetic acid] (Gee, et al., *J. Biol. Chem.* 1996;271(10):5768–5776). Gabapentin is a γ-aminobutyric acid (GABA) analogue. Gabapentin is effective in the treatment of epilepsy and in decreasing seizure frequency in both animal models and in human patients. The precise mechanism of action of gabapentin remains unclear. Recent experiments have shown that gabapentin also binds to the α2δ2 subunit.

Functional channels may be formed by expression of the calcium channel subunits in a cell. This technique is advantageous in determining the effects of various molecules on channel action. U.S. Pat. No. 5,712,158 and U.S. Pat. No. 5,770,447 describe a stable cell line that is useful for investigating gabapentin binding properties to calcium channel subunits. This cell line expresses the β subunit and the original α2δ subunit (now referred to as α2δ1) at high levels. Transfecting the cells with any α1 subunit results in the formation of functional calcium channels which can be used to evaluate the binding of gabapentin and gabapentin-related compounds.

It is the object of this invention to provide a new cell line that stably expresses a calcium channel α2δ2 subunit. It is a further object of this invention to describe α2δ2 subtype-specific binding of gabapentin, analogues of gabapentin, pregabalin, analogues of pregabalin, and 3-alkyl derivatives of GABA.

SUMMARY OF THE INVENTION

The invention provides a method for determining the binding ability of a compound to an α2δ2 subunit of a calcium channel comprising: providing an α2δ2 subunit of a calcium channel, contacting the α2δ2 subunit with the compound, and determining the binding ability of the compound to the α2δ2 subunit.

BRIEF DESCRIPTION OF THE DRAWINGS

FIG. 7. Scatchard Analysis of [³H]gabapentin (GBP) Binding to Membranes Form HEK293 Cells Overproducing Porcine α2δ1 (A) and Human α2δ2 (B). The cell membranes were prepared from GKS02, a stable cell line for porcine α2δ1, and GKS07, a stable cell line for human α2δ2. The specific [³H]gabapentin binding was carried out as described in Materials and Methods. The binding activity was expressed as pmole of gabapentin bound per mg of protein. Each binding reaction contained 20 μg of GKS02 membrane proteins or 10 μg of GKS07 membrane proteins. Data were averages of three assays.

DETAILED DESCRIPTION OF THE INVENTION

As used herein, analogues of gabapentin include but are not limited to alkyl-substituted gabapentin analogues, bridged gabapentin analogues, and heterocyclic gabapentin analogues such as those described by Bryans, et al. in *J. Med. Chem.* 1998;41:1838–1845. Analogues are defined as "compounds with similar electronic structures but different atoms" (Grant, et al., *Chemical Dictionary*, 5th ed., McGraw-Hill, 1987). Gabapentin has the structure:

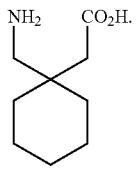

Examples of gabapentin analogues are described in Bryans, et al., supra, and include, but are not limited to:

A molecule with the structure:

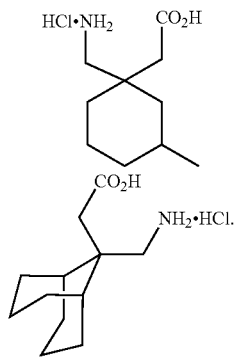

This analogue is alkylated at position 3 on the cyclohexane ring. An analogue may be alkylated at any position on a carbon ring with an alkyl group of from 1 to 4 carbon atoms. An analogue may also be a molecule with the structure:

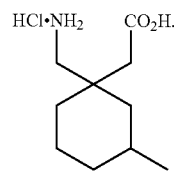

This analogue is alkyl-substituted at the 3-position of the gabapentin ring. Molecules of this type include pregabalin

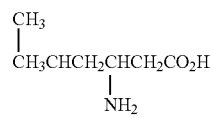

its analogues, and 3-alkyl derivatives of GABA.

MATERIALS AND METHODS

Porcine α2δ1 (pα2δ1) cDNA was from J. Brown (Brown J. P., Dissanayke V. U. K., Briggs A. R., Milic M. R, Gee N., *Anal. Biochem.*, 1998;255:236–243). Mouse α2δ3 (mα2δ3) cDNA was a generous gift from F. Hoffman (Klugbauer N., Lacinova L., Marais E., Hobom M., Hofmann F., *J. Neuroscl*, 1999;19:684–691). Monoclonal antibody against α2δ1 was purchased from Affinity Bioreagents, Inc. Polyclonal antibodies against α2δ2 and α2δ3 were from Sandra Duffy (Pfizer). Human and mouse multiple tissue blots and cDNA were purchased from CLONTECH. Mouse tissues were purchased from Pet-Freez Biologicals. PCR reagents were from Invitrogen. ECL Western blot kit was from Armersham. Lipofectamine, growth media, restriction enzymes were from LifeTechnologies. HEK293 and COS-7 cell lines were from ATCC. All other chemicals were from Sigma.

Cloning of human α2δ2 subunit. Human α2δ2 (hα2δ2) cDNA was amplified by PCR from a human brain cDNA library. Based on the deposited DNA sequence of hα2δ2 subunit from GenBank (accession number AF042792), four overlapped DNA fragments, which covered the whole open reading frame of hα2δ2 cDNA from nt −14 to 994 (fragment H), 845 to 1816 (fragment F), 1517 to 2791 (fragment D), and 2681 to 3790 (fragment C), were generated by PCR and then cloned into expression vector pcDNA3.1 by TA cloning kit. The sequences of the primer pairs used were:

5'-TCTTGAATGGAAACATGGCGGTGC-3' SEQ ID No. 1) and

5'-TATACCAGGGTCTCCTTCGGACAT-3' SEQ ID No. 2) (fragment H);

5'-ATGTGTTCATGGAAAACCGCAGAC-3' SEQ ID No. 3) and

5'-AGCCGTTCAGGTCAATGGCAAACA-3' SEQ ID No. 4) (fragment F);

5'-CCATCCGCATCAACACACAGGAAT-3' SEQ ID No. 5) and

5'-GTAAGTCCTCATTGTTAACCTCGC-3' SEQ ID No. 6) (fragment D);

5'-CTGAGAAGTTCAAGGTGCTAGCCA-3' SEQ ID No. 7) and

Figure 1:
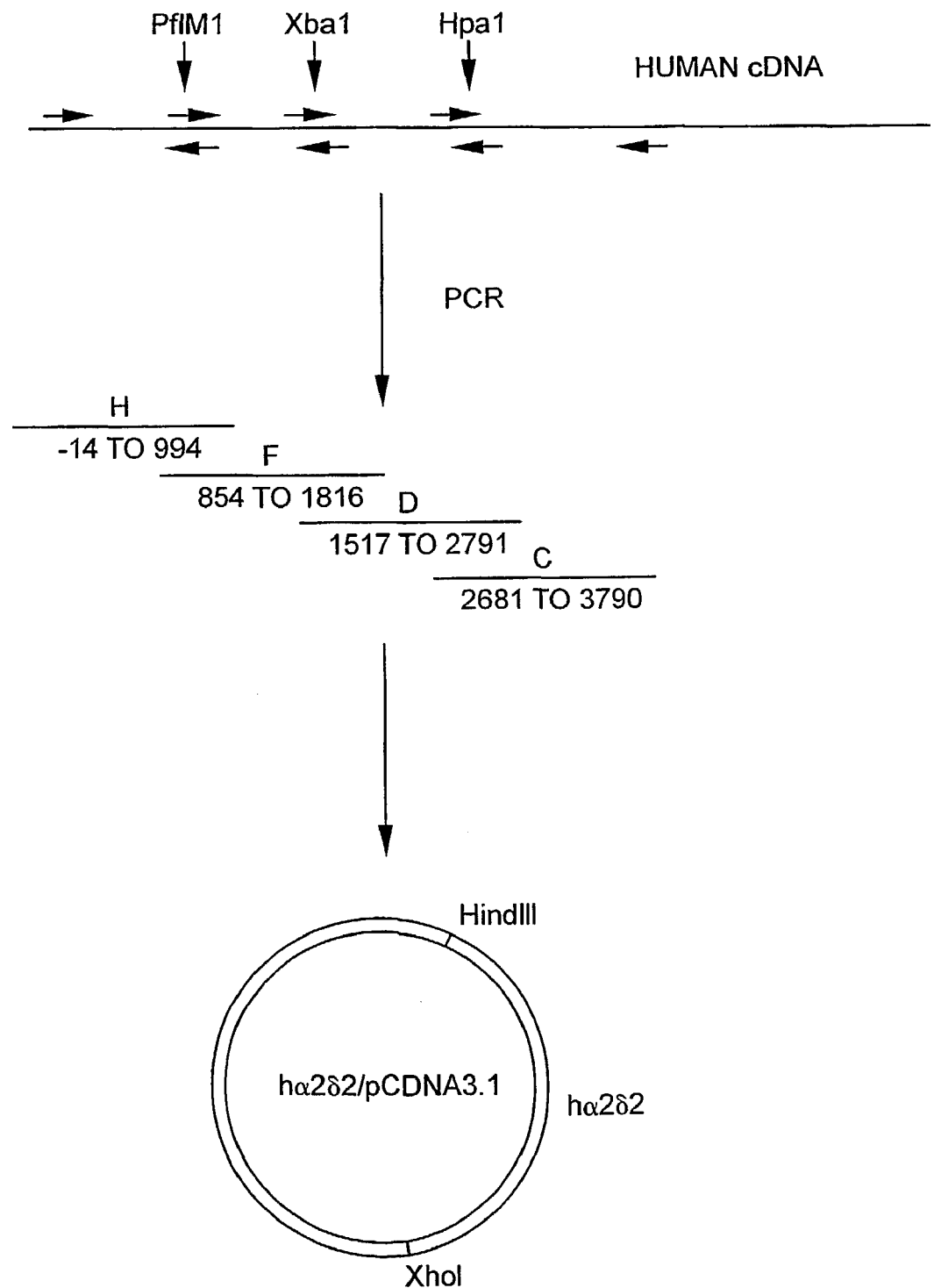
FIG. 1 diagrams the molecular cloning of human α2δ2 into the pCDNA3.1 expression vector.

5'-GATGTGATTTGGGTGCCAAACACC-3' SEQ ID No. 8) (fragment C). The four fragments were cut at internal unique restriction enzyme sites at nt 791 (PflM I), 1395 (Xba I), and 2628 (Hpa I), and assembled into pcDNA3.1 vector (Invitrogen, Carlsbad, Calif.) at Hind III/Xho I sites (see FIG. 1).

RT-PCR. Double-stranded cDNA preparations from different tissues (CLONTECH) were used for PCR reaction with 35 cycles at 94° C. for 1 minute, 55° C. for 1 minute, and 72° C. for 2 minutes. The reactions were performed in a solution containing 1 ng cDNA, 10 pM primers, 1 mM dNTPs, and 1×PCR buffer in a volume of 50 μL. Ten microliters of the reaction mix was loaded on 1% agarose gel. The primer pairs for human α8δ1, α2δ2, and α6δ3 were 5'-GACGCGGTGAATAATATCACAGCC-3' SEQ ID No. 9) and 5'-ACAAATCGTGCTTTCACTCCCTTG-3' nt 958 to 2165; accession number M76559) (SEQ ID No. 10);

5'-CTGAGAAGTTCAAGGTGCTAGCCA-3' SEQ ID No. 11) and

5'-GATGTGATTTGGGTGCCAAACACC-3' nt 2534 to 3643; accession number AF042792) (SEQ ID No. 12); and 5'-CGTGTCCTTGGCAGATGAATGGTC-3' SEQ ID No. 13) and 5'-CATCTCAGTCAGTGTCACCTTGAG-3' nt 1920 to 3272; accession number AJ272213) (SEQ ID No. 14), respectively. The expected lengths of PCR products from human α8δ1, α2δ2, and α6δ3 were 1208, 1110, and 1352 bp. These primers were specific for each subtype of α2δ as determined by sequencing analysis of the corresponding PCR products.

Northern blot analysis. Multiple Tissue Northern Blots (CLONTECH) were hybridized and washed according to the manufacturer's recommendation. Digoxigenin-labeled probes specific for subtypes of α2δ were generated by PCR and hybridized in 10 mL EasyHyb (Boehringer Mennhaim) at 50° C. overnight. The same pairs of primers as those used for RT-PCR were employed to generate the probes. The blots were washed twice, first in 2×SSC and 0.1% SDS at room temperature for 5 minutes, then in 0.1×SSC and 0.1% SDS at 68° C. for 15 minutes. Detection of expression was in accordance with the manufacturer's instructions (Boehringer Mennhaim).

Cell culture and transfection. COS-7 and HEK293 cells were cultured in DMEM and RPMI 1640 media, respectively. The media were supplemented with 50 units/mL penicillin, 50 μg/mL streptomycin, and 10% heat-inactivated fetal bovine serum (FBS), in a humidified incubator with 95% air and 5% $CO_2$ at 37° C. For transient transfection into COS-7 cells, 20 μg of plasmid DNA (vector or the same vector with α2δ insert) was incubated with 30 μL of lipofectamine. The mixture was overlaid onto the cells in 1.5 mL serum-free medium and incubated for 5 hours. Then FBS was added to the dishes to bring the final concentration to 10%. The medium was changed next morning. Forty-eight hours after the transfection, the cells were harvested for membrane preparation. For stable transfection of porcine α2δ1 and human α2δ2 into HEK 293 cells, the same procedure was applied as that for a transient transfection except for that 800 μg/mL G418 (gentacin) was added to the cells 48 hours after the transfection. Two clones, GKS02 and GKS07, showed highest expression of porcine α2δ1 and human α2δ2, respectively, and were selected for further binding studies. The cell line has ATCC No. PTA-1823. In addition, hosts for expression of α2δ2 protein binding assays can also include eukaryotic expression systems such as yeast, insect cells, and mammalian cells (CHO, COS-7, HEK293, etc.).

Membrane preparation. Membranes were prepared from tissues or cultured cells. The cells were washed twice with cold PBS and then scraped off with cold buffer containing Tris (5 mM, pH 7.4), EDTA (5 mM), PMSF (0.1 mM), leupeptin (0.02 mM), and pepstatin (0.02 mM). The cells were incubated on ice for 30 minutes, followed by sonication for 30 to 40 seconds. For membrane preparations from tissues, the tissues were sliced into small pieces and subjected to sonication at interval of 10 seconds 4 times. The resulting homogenates from tissues or cultured cells were centrifuged for 10 minutes at 750 to 1000×g, and then the supernatants were centrifuged at 50,000×g for 30 minutes. The resulting pellets were resuspended in the same buffer as described above.

Western blot analysis. The cell membranes (0.5 μg for GKS07 cells, 5 μg for GKS02 cells, 100 μg for transiently transferred cells or tissues) were resolved by 4% to 20% SDS-PAGE and transferred to nitrocellulose membranes using semi-dry transferring unit. The membranes were incubated with either rabbit anti-α2δ1, α2δ2, and α2δ3 antibodies for 1 hour at room temperature, followed by washing with 1×PBS. The blots were incubated with anti-rabbit IgG for 1 hour and developed with ECL reaction according to the procedure recommended by manufacturer.

Binding assays. The radioligand-binding assay was done using membrane proteins incubated in the presence of 20 nM [$^3$H]gabapentin. The membranes (100 μg of proteins for transiently transfected cells, 20 μg for GKS02 cell membranes, and 10 μg for GKS07 cell membranes) were incubated in 10 mM HEPES (N-[2-hydroxyethyl]piperazine-N'-[2-ethanesulfonic acid]) (pH 7.4) for 40 to 50 minutes at room temperature, and then filtered onto pre-wetted GF/C membranes and quickly washed five times with 3 mL of ice cold 50 mM Tris buffer (pH 7.4). The filters were dried and counted in a liquid scintillation counter. For determining nonspecific binding, the binding assays were performed in the presence of 10 μM pregabalin (Gee N. S., Brown J. P., Dissanayake V. U., Offord J.; Thurlow R., Woodruff G. N., J. Biol. Chem., 1996;271:5768–5776). The specific binding was obtained by subtracting nonspecific binding from the total binding. Clone #7 was identified as the highest α2δ2 subunit expressing clone. Binding assays can also be performed using recombinant and/or purified α2δ2 protein from human and other mammalian species, for screening α2δ2 subtype-selective inhibitors.

RESULTS

Figure 2:
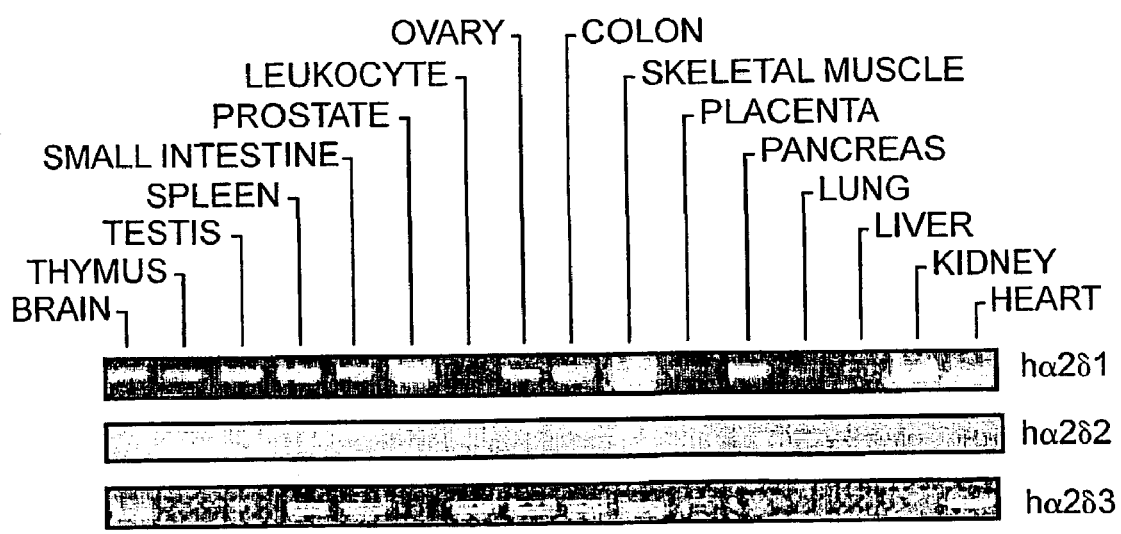
FIG. 2. RT-PCR Analysis of Human α2δ Tissue Distribution. One ng of double-stranded cDNA from different human tissues (CLONTECH) was amplified by PCR with 35 cycles of 94° C. for 1 minute, 55° C. for 1 minute, and 72° C. for 2 minutes. The generated PCR products represent DNA fragments from nucleotide 958 to 2165 (hα2δ1), 2534 to 3643 (hα2δ2), and 1920 to 3272 (hα2δ3).
Figure 3A:
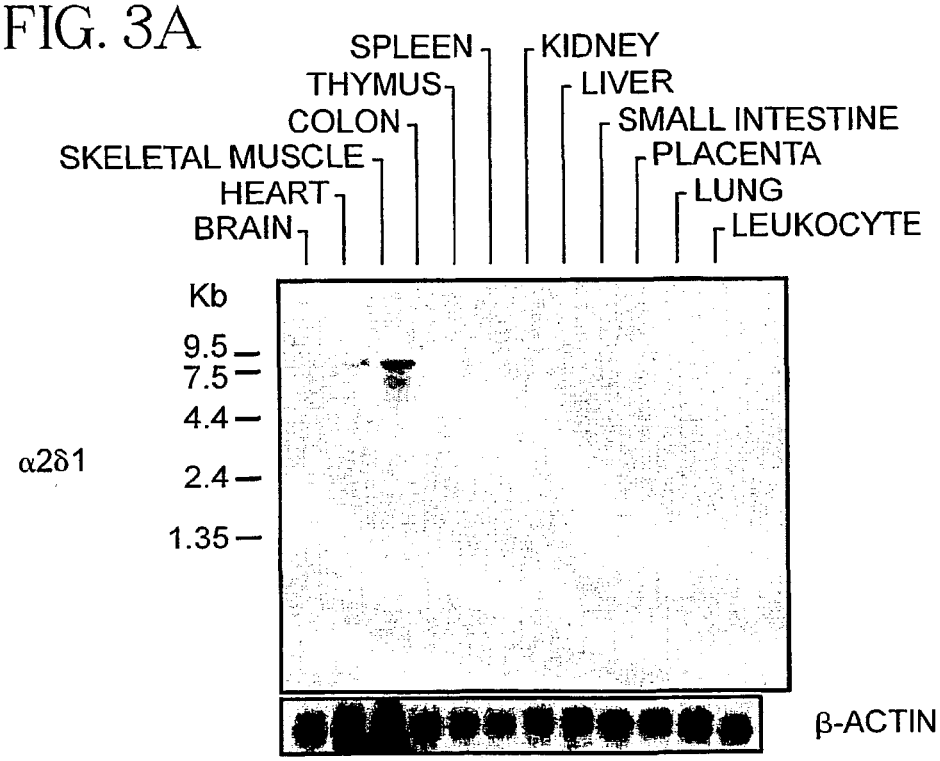
FIG. 3A–F Northern Blot Analysis Human α2δ Tissue Distribution. Northern blotting was carried out as described in Materials and Methods. Human multiple tissue blots (CLONTECH) were hybridized with Digoxigenin-labeled cDNA synthesized from nucleotide 958 to 2165 (h α2δ1), 2534 to 3643 (h α2δ2), and 1920 to 3272 (h α2δ3). The positions of marker RNA are indicated to the left.
Figure 3B:
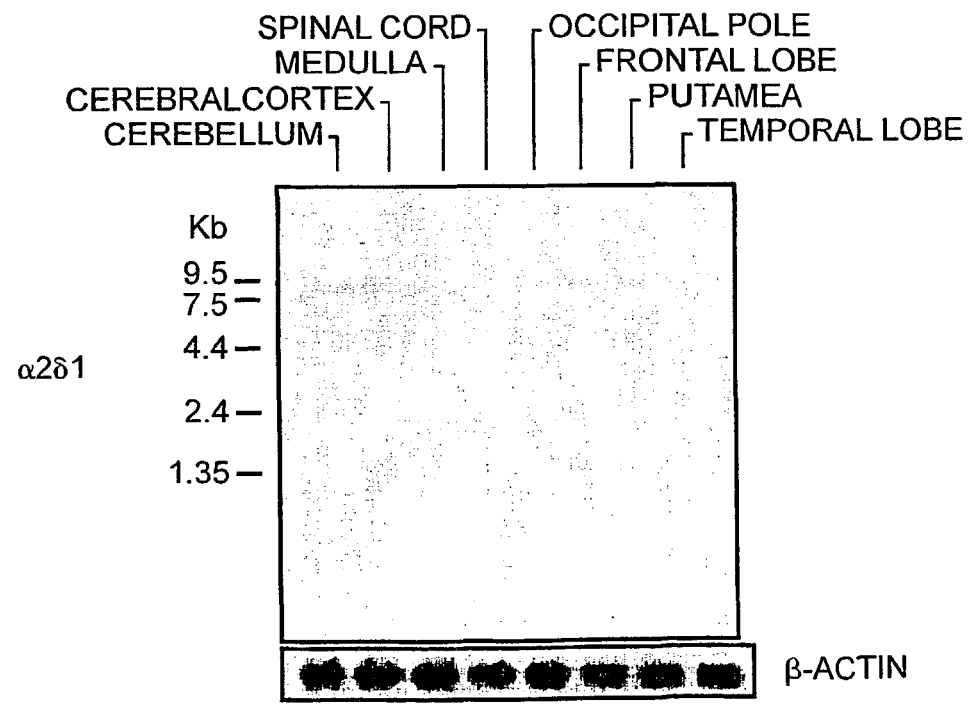
Figure 3C:
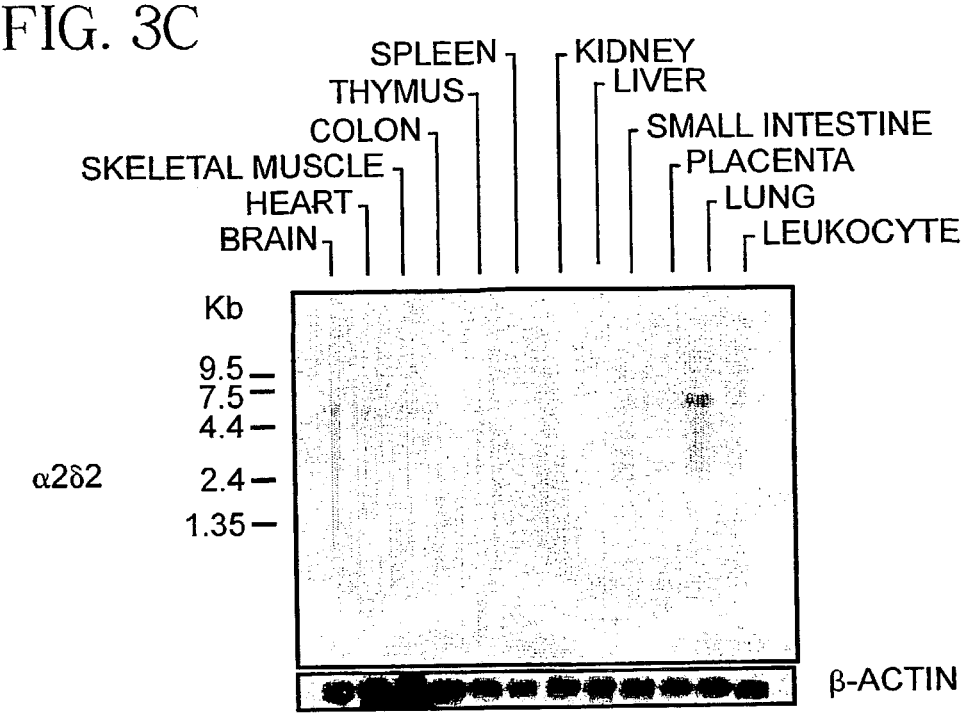
Figure 3D:
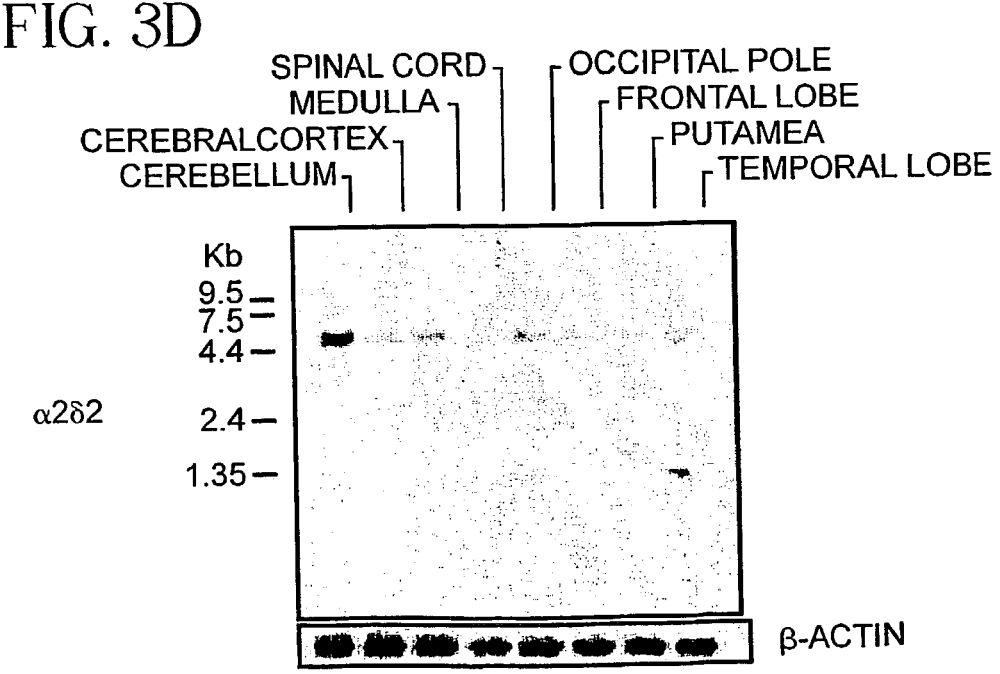
Figure 3E:
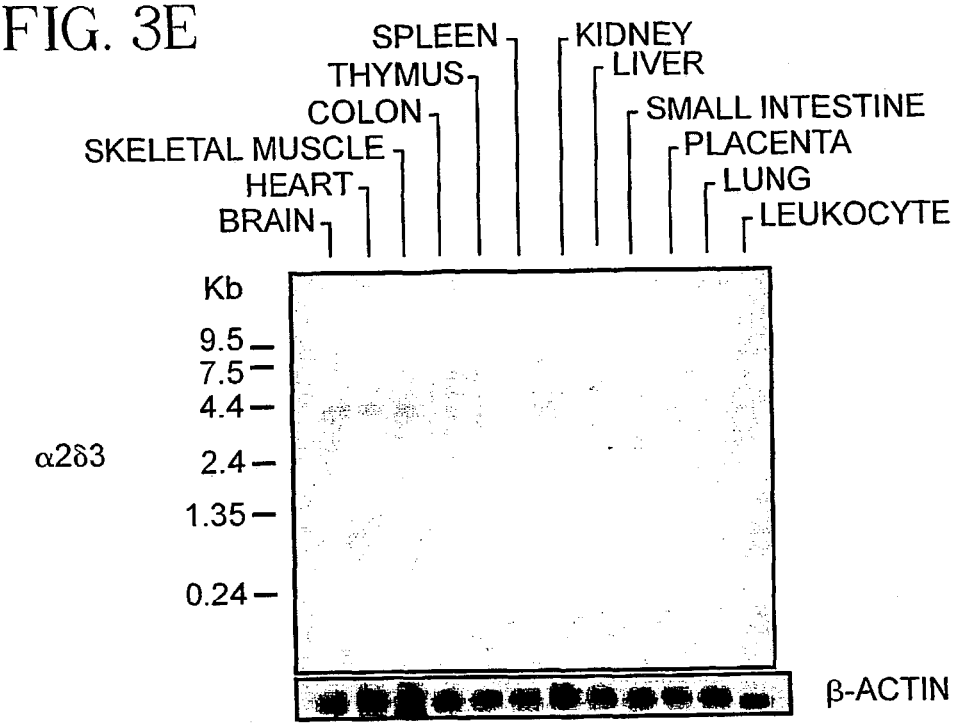
Figure 3F:
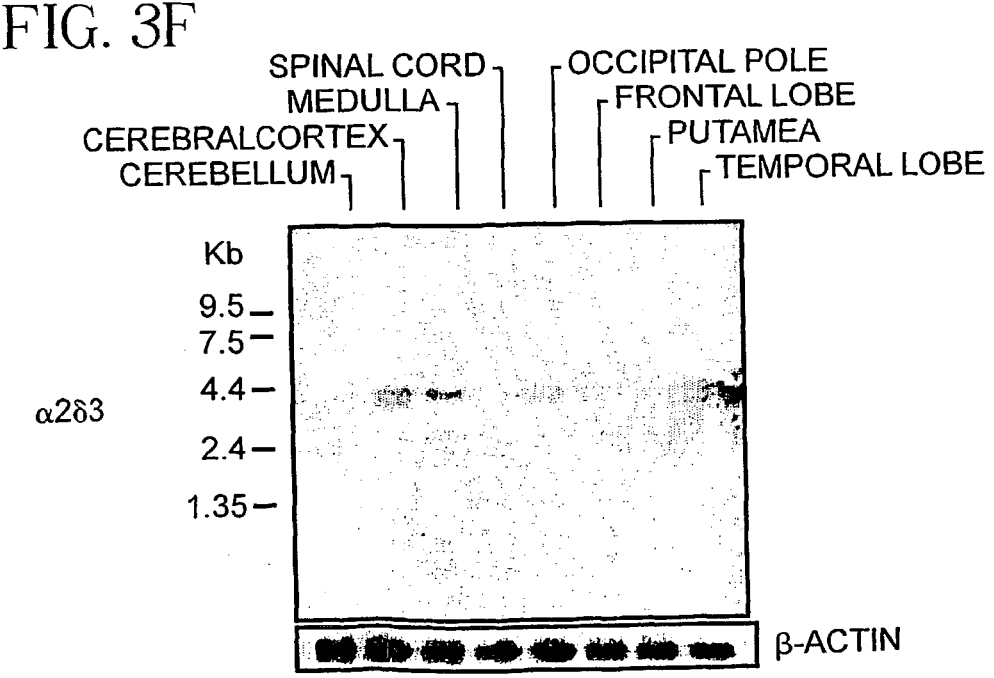

Tissue distribution of α2δ transcripts. Tissue distribution of hα2δ1, hα2δ2, and hα2δ3 mRNA was first examined by RT-PCR analysis. These probes were designed to specifically amplify three subtypes of α2δ. As shown in FIG. 2, single PCR products corresponding well to the predicted sizes of hα2δ1, hα2δ2, and hα2δ3 (1208, 1110, and 1352 bp) appeared in almost all tissues tested. A much higher level of hα2δ2 transcript was found in lung than any other tissues including brain. Since the PCR products showed sequences identical to the corresponding α2δ, the wide scope of tissue distribution revealed the ubiquitous feature of hα2δ mRNA expression. However, the RT-PCR condition used here did not yield quantitative estimation of 2δ mRNA levels among different tissues, Northern analysis is necessary for estimating the relative abundance of each subtype of hα2δ mRNA. Northern blots demonstrated that all three hα2δ genes were expressed about equally well in brain, heart, and skeletal muscle except for the much higher expression of hα2δ1 in skeletal muscle (FIG. 3). In addition to these three tissues, the most abundant hα2δ2 transcript was found in lung. The highest expression of hα2δ2 mRNA in lung was consistent with the above described RT-PCR results and also agreed well with one recent report (Gao B., Sekido Y., Maximov A., Saad M., Forgacs E., Latif F., et al., *J. Biol. Chem.*, 2000; 275:12237–12242), but differed from an early observation (Klugbauer N., Lacinova L., Marais E., Hobom M., Hofmann, F., *J. Neurosci.*,1999;19:684–691). In the present study we also detected a small amount of hα2δ1 and hα2δ3 mRNAs in liver and kidney, respectively. Results from this and other laboratories (Klugbauer, Supra., 1999; Gao, Supra., 2000, and our unpublished data) have shown that expression of mouse α2δ3 (mα2δ3) is restricted to the brain. The expression of hα2δ3 also in tissues other than brain suggested species difference in 2δ3 expression.

In the brain, hα2δ1, hα2δ2, and hα2δ3 were detected in every portions of brain tissues tested including cerebellum, cerebral cortex, medulla, occipital pole, frontal lobe, temporal lobe, and putamen. A higher level of hα2δ2 transcript was found in cerebellum than cerebral cortex, while reverse was true for hα2δ3. For hα2δ1, its mRNA was approximately equally distributed in these two regions. The expression patterns of the three isoforms in these two brain regions were in accordance with previous in situ hybridization results (Klugbauer, Supra., 1999; Hobom M., Dai S., Marais E., Lacinova L., Hofmann F., Klugbauer N., *Eur. J. Neurosci.*, 2000;12:1217–1226). In addition, all three subtypes of 2δ mRNA were found in spinal cord, but at lower levels than that found in the brain.

Figure 4A:
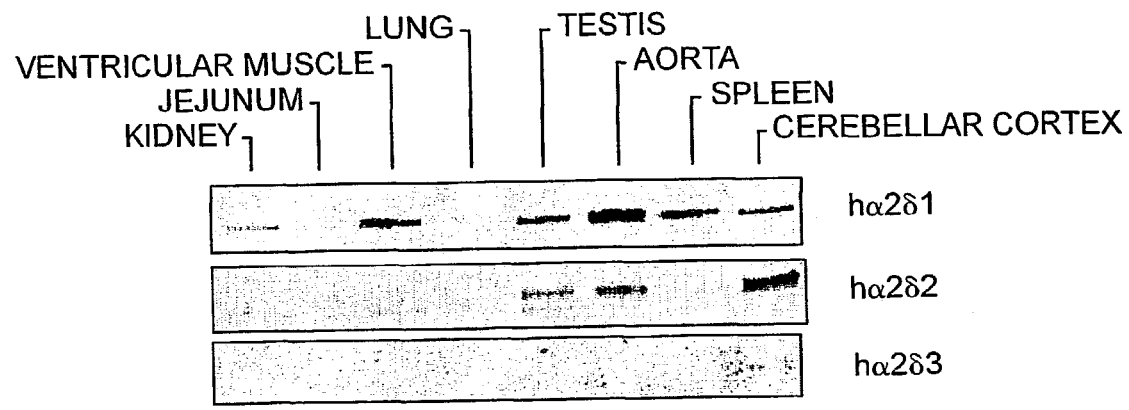
FIG. 4A–B Western Blot Analysis of Human and Mouse .alpha.2.delta. Tissue Distribution. Membrane proteins from different human tissues (A, 0.5 μg) and mouse tissues (B, 100 μg) were loaded on 4% to 20% SDS-PAGE (NOVEX) and subjected to Western blot analysis (see Materials and Methods). The blots were probed with anti-α2δ monoclonal antibody or polyclonal antibodies against α2δ2 and α2δ3.
Figure 4B:
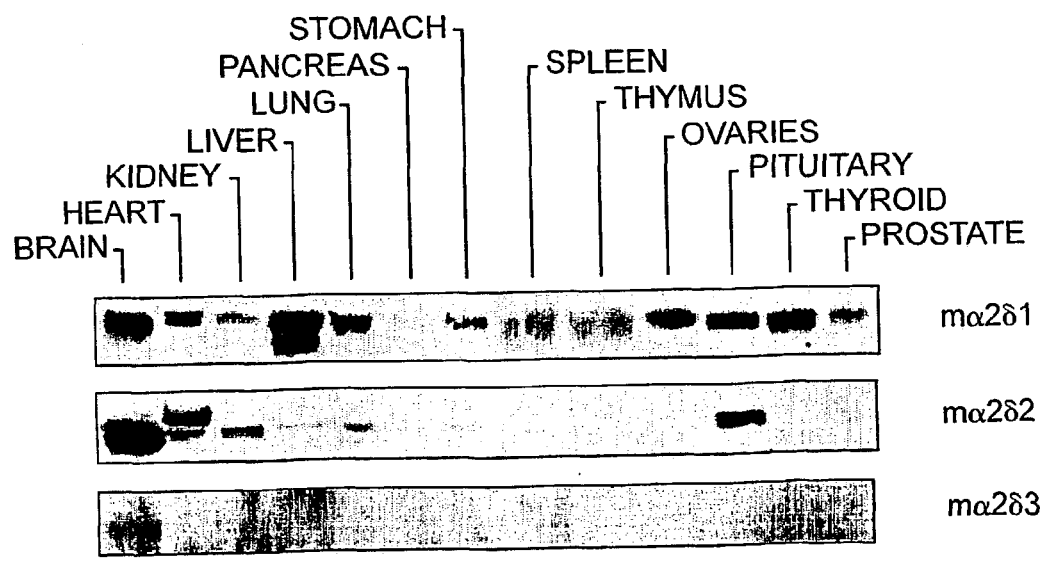

Tissue distribution of 2δ proteins. Although the level of protein is function of the steady-state level of mRNA, the relative abundance of mRNA and protein of specific gene is not always proportional, which may reflect post transcriptional regulation (Jackson V. N., Price N. T., Carpenter L., Halestrap A. P., *Biochem. J.*, 1997;324:447–453). To examine the relative levels of human and mouse 2δ subunits across tissues, we used antibodies raised against specific subtypes of 2δ protein for Western analysis. Equal amounts of proteins were loaded on SDS polyacrylamide gels. Consistent with the ubiquitous distribution of hα2δ1, Western blots of human and mouse tissues showed that both hα2δ1 and mα2δ1 proteins were widely distributed, although hα2δ1 in lung and jejunum were not detectable. By contrast, hα2δ3 protein was only detected in brain, not in lung, testis, aorta, spleen, jejunum, and kidney (FIG. 4A). Similarly, mα2δ3 protein was found only in brain, not in heart, kidney, liver, lung, pancreas, stomach, spleen thymus, ovary, pituitary, thyroid, and prostate. Surprisingly, in contrast to predominant expression of hα2δ2 transcript in lung (FIGS. 2 and 3), hα2δ2 protein was predominantly found in brain and the level of hα2δ2 protein was not detectable in lung (FIG. 4A). In addition to brain, low levels of hα2δ2 protein were also found in aorta, testis, and ventricular muscle. There seemed to be two immunoreactive bands in testis with one equivalent to predicted molecular weight of hα2δ2 (175 kDa) and the other showing slightly lower molecular weight. This lower molecular protein appeared to be similar to the predominant band detected in ventricular muscle. As previously observed with pα2δ1, this lower band may represent the dissociated α2 subunit from the α2δ protein or an isoform of α2δ2 (Brown J. P., Dissanayke V. U. K., Briggs A. R., Milic M. R., Gee N., *Anal. Biochem.*, 1998;255: 236–243; Wang M., Offord J., Oxender D. L., Su, T. Z., *Biochem. J.*, 1999;342:313–320). In addition, two immunoreactive bands were also detected in mouse heart by anti-α2δ2 antibodies, but the predominant band in this case had molecular weight higher than that found in other tissues (FIG. 4B).

Figure 6:
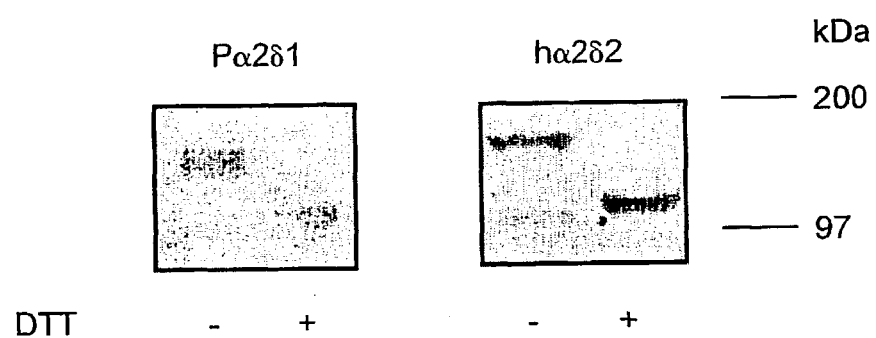
FIG. 6. Disruption of Disulphide-Linkage Between α2 and δ Subunits. An equal amount of membrane protein from each sample (0.5 μg for pα2δ1 and 5 μg for hα2δ2) was incubated in the presence or absence of 100 mM DTT for 10 minutes and resolved on a nonreducing SDS-PAGE and transferred to a PVDF membrane. The blots were probed with either an anti-α2δ1 antibody (left) or an anti-α2δ2 antibody (right). The positions of marker proteins are indicated to the right.

Disulphide linkage of α2 and δ proteins. It has been shown that α2 and δ subunits of α2δ1 were linked by disulphide bond (Wang, Supra., 1999). Since the amino acid sequence in δ region is less conserved between α2δ1 and α2δ2, it is interesting to know if α2δ2 protein is also cleaved into two subunits post translation. To examine such a possibility, cell membranes from HEK 293 cell lines overproducing pα2δ1 (GKS02) and hα2δ2 (GKS07) proteins were treated or untreated with 100 mM DTT before gel electrophoresis. In the presence of DTT, both pα2δ1 and hα2δ2 proteins were shifted to a position predicted for α2, suggesting that as with pα2δ1, hα2δ2 also consists of two subunits that are linked by disulphide bond (FIG. 6).

Figure 5:
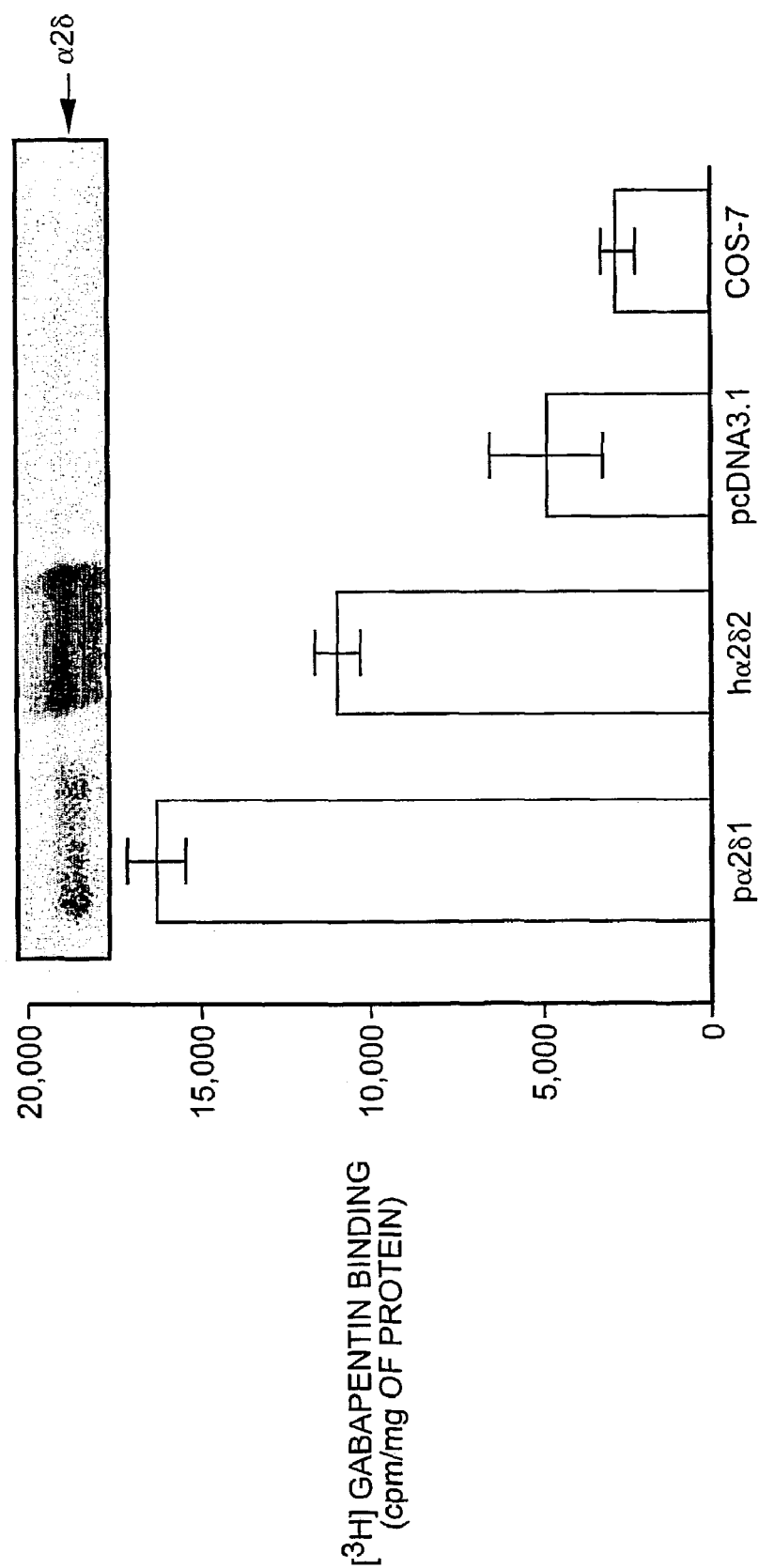
FIG. 5. Binding of [³H] Gabapentin to Membranes From COS-7 Cells Transfected With α2δ cDNA. COS-7 cells were transfected with 20 μg of pcDNA3.1 (control), pcDNA3.1/porcine α2δ1 construct (pα2δ1), and pcDNA3.1 //human α2δ2 construct (hα2δ2). The membranes were prepared for [3H]gabapentin binding assays (see Materials and Methods). Data are an average of three independent assays with triplet in each determination. The same membranes (100 μg) were subjected to Western blot analysis with corresponding antibodies as described in Materials and Methods.

[$^3$H]Gabapentin Binding. To determine the gabapentin binding properties of the cloned hα2δ2, membranes were isolated from COS-7 cells transiently transfected with pα2δ1, hα2δ2, and vector pcDNA3.1. Expression of the corresponding α2δ proteins was examined by Western blots. As shown in FIG. 5, transfection of the cells with pα2δ1 resulted in a prominent increase in gabapentin binding. Similarly, the cells expressing hα2δ2 exhibited about four-fold increase in gabapentin-binding activity. Although a slightly increased binding; activity was observed in the cells transfected with pcDNA3.1 vector alone, statistic analysis did not show that this smaller change was significant.

Gabapentin binding$K_D$ and the binding properties of pα2δ1 and hα2δ2 were determined in cell lines GSK02 (pα2δ1) and GKS07 (hα2δ2). In HEK293 cells stably expressing pα2δ1, [$^3$H]gabapentin bound to a single population of sites as demonstrated in previous report (Gee, Supra., 1996) with$K_D$ value of 72±9 nM (FIG. 7A). Similarly, a single population of binding sites were also observed in hα2δ2-containing membranes (FIG. 7B), but the $K_D$ value was higher than that of pα2δ1 (156±25 nM). To determine pharmacological properties of hα2δ2, several compounds were selected for competition with [$^3$H]gabapentin binding. A similar, but not identical profile of competition was seen in the two subtypes of α2δ protein (Table 1). For instance, binding to both subtypes of α2δ were stereo-selective because L-leucine was markedly more potent than its D-enantiomer. The affinities of BCH, a model substrate of system L transport (Su T. Z., Lunney E., Campbell G., Oxender D. L., *J Neurochem.*, 1995;64:2125–2131), and phenylalanine were weak for both subtype proteins. On the other hand, gabapentin binding to α2δ2 was more sensitive to (S+)-3-isobutyl GABA (pregabalin) with IC$_{50}$ value of 96 nM as compared to 149 nM for pα2δ1.

TABLE 1

IC$_{50}$ Values for Inhibition of [$^3$H]Gabapentin Binding to Membranes From Stable Cell Lines Overproducing Porcine α2δ1 (GKS02) and Human α2δ2 (GKS07) by Selected Amino Acids

| Compounds | GKS02 (pα2δ1) | GKS07 (hα2δ2) |
| --- | --- | --- |
| Gabapentin | 132 | 282 |
| Pregabalin | 149 | 96 |
| L-leucine | 118 | 205 |
| L-phenylalanine | 825 | 2,960 |
| D-leucine | 198,960 | 151,510 |
| BCH | 1,028 | 775 |

Figure 8:
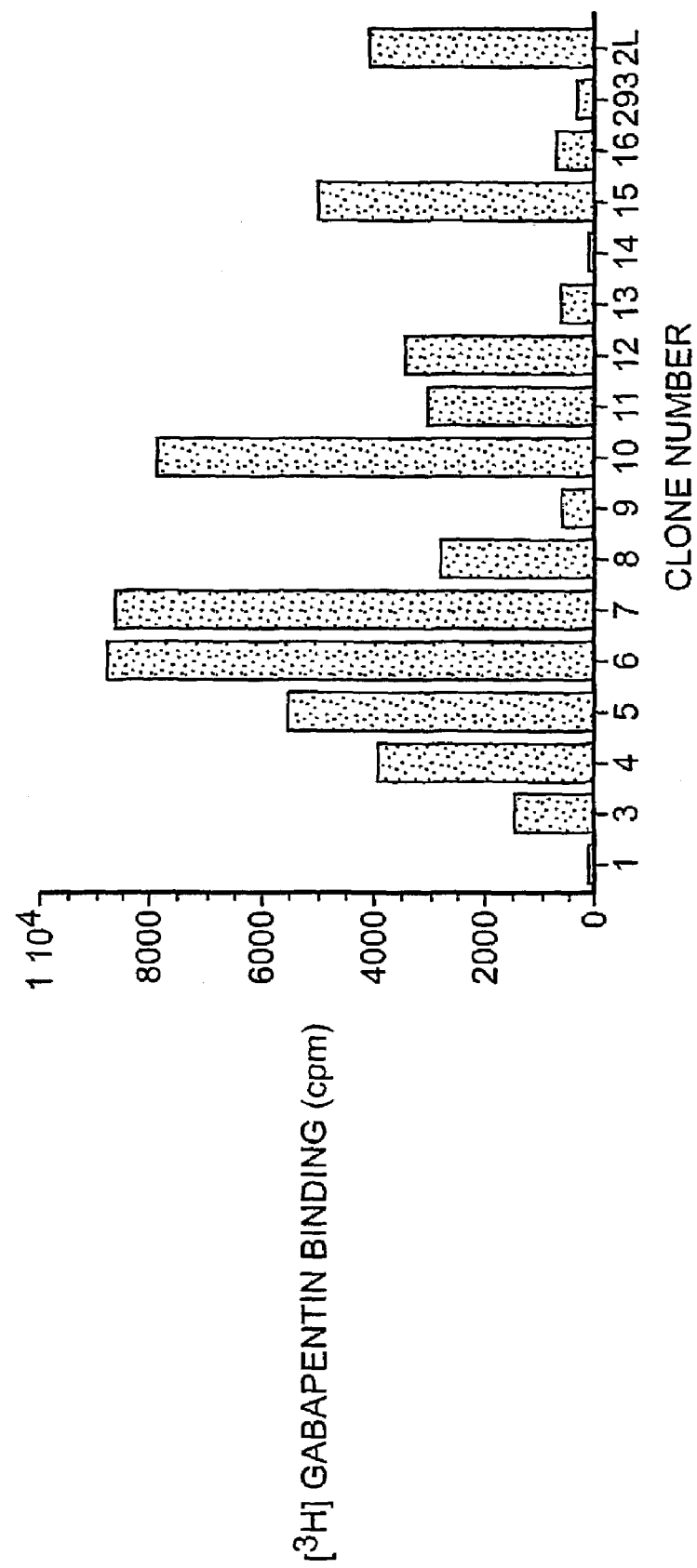
FIG. 8. Screening Cell Lines by [³H] Gabapentin (GBP) Binding Activity. HEK293 cells were transferred with human α2δ2. Single clones were selected by G418-resistance. "2923," parental cells HEK293; "2L," BEK293 cells stably expressing porcine α2δ1.

FIG. 8 also illustrates the screening of stable cell lines that express human α2δ2 protein.

While the forms of the invention herein disclosed constitute presently preferred embodiments, many others are possible. It is not intended herein to mention all of the possible equivalent forms or ramifications of the invention. It is understood that the terms used herein are merely descriptive, rather than limiting, and that various changes may be made without departing from the spirit or scope of the invention.

What is claimed is:

1. A method for determining the binding ability of a compound to a cell expressing an α2δ2 subunit of a calcium channel comprising providing a cell line expressing an α2δ2 sub-unit of a calcium channel, said cell line having ATCC No. PTA-1823; contacting the cells with the compound; and determining the binding ability of the compound to the cells.

2. The method of claim 1 wherein the compound is gabapentin.

3. The method of claim 1 wherein the compound is a 3-alkyl substituted gabapentin.

4. The method of claim 1 wherein the compound is pregabalin.

5. The method of claim 1 wherein the compound is a 3-alkyl derivative of γ-aminobutiric acid (GABA).

6. A cell line having ATCC No. PTA-1823.

7. A method for determining the binding ability of a compound to an α2δ2 subunit of a calcium channel comprising; providing an α2δ2 subunit of a calcium channel encoded by the nucleotide sequence set forth in accession NO. AF 042792; contacting the α2δ2 subunit with the compound; and determining the binding ability of the compound to the α2δ2 subunit.

8. The method of claim 7 wherein the compound is gabapentin.

9. The method of claim 7 wherein the compound is a 3-alkyl substituted gabapentin.

10. The method of claim 7 wherein the compound is pregabalin.

11. The method of claim 7 wherein the compound is a 3-alkyl derivative of GABA.

12. The method of claim 7 wherein the α2δ2 subunit is a purified protein.

* * * * *